US009645056B2

(12) United States Patent
Kasamatsu

(10) Patent No.: US 9,645,056 B2
(45) Date of Patent: May 9, 2017

(54) PRETREATMENT SOLUTION FOR IMMUNOHISTOCHEMICAL STAINING AND CONDENSED SOLUTION THEREOF

(71) Applicant: NICHIREI BIOSCIENCES INC., Tokyo (JP)

(72) Inventor: Toshiyuki Kasamatsu, Higashimurayama (JP)

(73) Assignee: NICHIREI BIOSCIENCES, INC., Tokyo (JP)

( * ) Notice: Subject to any disclaimer, the term of this patent is extended or adjusted under 35 U.S.C. 154(b) by 0 days.

(21) Appl. No.: 14/299,166

(22) Filed: Jun. 9, 2014

(65) Prior Publication Data

US 2014/0287429 A1    Sep. 25, 2014

Related U.S. Application Data

(63) Continuation of application No. 13/576,880, filed as application No. PCT/JP2011/052228 on Feb. 3, 2011, now abandoned.

(30) Foreign Application Priority Data

Feb. 5, 2010 (JP) ................. 2010-024784

(51) Int. Cl.
  *G01N 1/30* (2006.01)
  *G01N 33/53* (2006.01)

(52) U.S. Cl.
  CPC ........... *G01N 1/30* (2013.01); *G01N 33/5306* (2013.01)

(58) Field of Classification Search
  CPC ............................ G01N 33/5306; G01N 1/30
  See application file for complete search history.

(56) References Cited

U.S. PATENT DOCUMENTS

| | | |
|---|---|---|
| 6,296,809 B1 | 10/2001 | Richards et al. |
| 6,451,551 B1 | 9/2002 | Zhan et al. |
| 6,649,368 B1 | 11/2003 | Aghassi et al. |
| 7,883,864 B2 | 2/2011 | Fujisato et al. |
| 8,288,122 B2 * | 10/2012 | O'Leary .............. A01N 1/0231 435/40.52 |
| 2003/0175852 A1 | 9/2003 | Kalra et al. |
| 2005/0118725 A1 | 6/2005 | Towne et al. |
| 2005/0226922 A1 | 10/2005 | Ameri et al. |

FOREIGN PATENT DOCUMENTS

| | | |
|---|---|---|
| CN | 1238042 A | 12/1999 |
| CN | 1325123 C | 7/2007 |
| EP | 0 935 139 B1 | 11/2004 |
| JP | 2001-505297 A | 4/2001 |
| JP | 2003-526086 A | 9/2003 |
| JP | 2004-515752 A | 5/2004 |
| WO | 95/24498 A1 | 9/1995 |
| WO | 00/14507 A1 | 3/2000 |

OTHER PUBLICATIONS

Hiroyuki Nishimura, et al., "Consideration of Dewaxing Process", The Journal of Japanese Medical Instruments, Nov. 1, 2005, pp. 741-745, vol. 75, No. 11.
Shinji Hamakawa, et al., "Kateiyo Senzai o Mochiita Kanetsu Shori ni yoru Datsu-Paraffin Oyobi Kogen Fukatsu Doji Shori no Kento", Byori Gijutsu, 2003, pp. 10-14, vol. 66.
"Koso Koutai Hou" (Immunoenzymatic technique), Revised 4th Edition, Watanabe and Nakane, Kakusai Kikaku (2002), 4 pages.
International Searching Authority, International Preliminary Report on Patentability issued in corresponding International Application No. PCT/JP2011/052228, dated Sep. 18, 2012.
European Patent Office, European Search Report issued in corresponding EP Application No. 11739816.4, dated Jul. 31, 2013.

* cited by examiner

*Primary Examiner* — Shafiqul Haq
(74) *Attorney, Agent, or Firm* — Sughrue Mion, PLLC

(57) ABSTRACT

Disclosed are a pretreatment solution for immunohistochemical staining, which elutes a paraffin-containing embedding medium from a glass slide with a tissue specimen embedded in the medium, and retrieves antigenicity of the tissue specimen, and which is usable three or more times, and a pretreatment solution concentrate for immunohistochemical staining which allows ready preparation of the pretreatment solution and a method of immunohistochemical staining using the same. The pretreatment solution contains an antigen retrieving agent, particular nonionic surfactants, and cyclodextrin or a derivative thereof, with the balance being not less than 80 mass % of water. The content of the antigen retrieval agent is such that the pH of the pretreatment solution is in a predetermined range, and the content of cyclodextrin or a derivative thereof is a particular amount.

14 Claims, No Drawings

PRETREATMENT SOLUTION FOR IMMUNOHISTOCHEMICAL STAINING AND CONDENSED SOLUTION THEREOF

CROSS-REFERENCE TO RELATED APPLICATIONS

This is a continuation of U.S. application Ser. No. 13/576,880 (pending), filed Aug. 2, 2012, which is a 371 National Stage Application of PCT/JP2011/052228 filed Feb. 3, 2011, which claims benefit of Japanese Application No. 2010-024784 filed Feb. 5, 2010. The above applications are incorporated herein by reference in their entirety.

FIELD OF ART

The present invention relates to a pretreatment solution and a solution concentrate thereof for immunohistochemical staining, which solution allows immunohistochemical staining to be conducted in a short time and with less labor, the immunohistochemical staining including: eluting a paraffin-containing embedding medium from a glass slide with a tissue specimen as an antigen embedded in the medium; antigen retrieving; washing; reacting with an antibody; and staining. In particular, the present invention relates to a pretreatment solution and a solution concentrate thereof for immunohistochemical staining, which solution functions both to elute a paraffin-containing embedding medium for immunohistochemical staining from a glass slide with a tissue specimen embedded in the medium and to retrieve antigenicity, which allows for sufficient staining intensity in the subsequent immunohistochemical staining, and which maintains the eluted embedding medium dispersed therein even after its first use, and is capable of being used three or more times.

BACKGROUND ART

In pathology, deparaffinization and antigen retrieval pretreatment for immunohistochemical staining of a glass slide with a tissue specimen usually includes, as described in Non-patent Publication 1: the first step of deparaffinization by passing a formalin-fixed paraffin-embedded tissue section through an organic solvent layer, such as xylene, benzene, or toluene, three times for three-minutes each; the second step of rehydration of the glass slide and the tissue specimen by passing them through an amphiphilic solution, such as ethanol, four times for three-minutes each; and the third step of antigen retrieval of the rehydrated tissue specimen by heat treating the rehydrated tissue specimen immersed in an antigen retrieval solution, such as a citrate buffer or a Tris-EDTA solution.

The organic solvents used in the first step of the pretreatment, such as xylene, benzene, or toluene, are highly toxic and volatile, which requires exhaust equipment such as draft, and disadvantageously affects the environment of engaged technicians.

As a substitute for the disadvantageous organic solvents, highly safe deparaffinization agents are commercially available, such as Hemo-De (trade name, manufactured by FALMA), an organic solvent extracted and purified from citrus peels, Clear-Plus and Hemo-Clear (both trade names, manufactured by FALMA) using aliphatic hydrocarbon (alkanes), and Tissue Clear (trade name, manufactured by SAKURA FINETEK JAPAN CO., LTD.).

Rather than using the highly safe deparaffinization agents, more convenient methods are desired wherein the three steps of the pretreatment are performed simultaneously in a single solution, and some proposals have been made.

For example, Patent Publication 1 proposes a pretreatment process wherein deparaffinization and antigen retrieval are performed simultaneously by heating, to a temperature higher than the melting point of paraffin, a paraffin-embedded tissue specimen in a solution containing a paraffin-solubilizing organic solvent selected from aromatic hydrocarbon, a terpene, or isoparaffinic hydrocarbon, a polar organic solvent, an antigen retrieving component, and a surfactant. Patent Publication 1 also discloses that, for removing residual surfactant in a washing step following the pretreatment process, cyclodextrin, which binds to the surfactant, may be contained in the washing solution.

On the other hand, Patent Publication 1 discloses in Example 7 that, when the above-mentioned solution used in the pretreatment is used consecutively, the residual paraffin eluted in the solution after the pretreatment adheres to a next slide, so that this solution is not suitable for consecutive use.

Further, when a solution of the composition disclosed in Patent Publication 1 is made to have an alkaline pH, in the immunohistochemical staining following the pretreatment, the glass slide with the tissue specimen adhered thereto is prone to repel the staining reagent at portions free of the tissue specimen, resulting in uneven staining.

Patent Publications 2 and 3 disclose that deparaffinization and antigen retrieval may be effected simultaneously using a solution containing various buffers, surfactants, ethylene glycol, and the like, in the same way as the pretreatment process disclosed in Patent Publication 1.

However, in these publications, consecutive use of the pretreatment solution is not intended either, similarly to the solution of Patent Publication 1, and there is no description of a technology such as for dispersing the eluted paraffin in the solution, or the like. Thus it is likely that the pretreatment solutions disclosed in these publications, when used consecutively, also have the same problems as that of Patent Publication 1.

Incidentally, some pretreatment solutions for immunohistochemical staining which effect deparaffinization and antigen retrieval simultaneously are already in the market, such as those disclosed in the above patent publications, including Trilogy (trade name, manufactured by Cell Marque Corporation) for single use, or Target Retrieval Solution pH9 (3-in-1) (trade name, manufactured by DAKO) for use three consecutive times within a week.

The compositions of these commercial products are not known, but do not contain cyclodextrin. Further, in all of such products, hydrophobic paraffin eluted into the pretreatment solution during use often floats on the solution surface.

Such insoluble paraffin on the solution surface adheres to a glass slide with a tissue specimen when it is taken out of the solution, so that more washing steps are required before the subsequent staining, which complicates the operation. Otherwise, the insoluble paraffin adversely affects the subsequent immunohistochemical staining. Further, when staining is performed in an automatic immunohistochemical stainer, the insoluble paraffin may adversely affect the stainer.

PRIOR ART PUBLICATIONS

Patent Publications

Patent Publication 1: JP-2001-505297-A
Patent Publication 2: JP-2003-526086-A
Patent Publication 3: U.S. Pat. No. 6,649,368-B1

Non-Patent Publications

Non-Patent Publication 1: "*Koso Koutai Hou*" (Immunoenzymatic technique), Revised 4th Edition, Watanabe and Nakane, Kakusai Kikaku (2002)

SUMMARY OF THE INVENTION

Problems to be Solved by the Invention

It is an object of the present invention to provide a pretreatment solution for immunohistochemical staining which functions in immunohistochemical staining both to elute a paraffin-containing embedding medium from a glass slide with a tissue specimen in the form of a sliced tissue section adhered to the slide and embedded in the medium, and to retrieve antigenicity of the tissue specimen, which allows for sufficient staining intensity in the subsequent immunohistochemical staining, which maintains the eluted embedding medium dispersed therein even after its first use, which is usable three or more consecutive times, and which is excellently safe.

It is another object of the present invention to provide a pretreatment solution for immunohistochemical staining, which solves the above problems, and which, upon staining subsequent to the elution of a paraffin-containing embedding medium from a glass slide with a tissue specimen in the form of a sliced tissue section adhered to the slide and embedded in the medium, and the antigen retrieval of the tissue specimen, inhibits a staining reagent from being repelled on the portion of the glass slide without the tissue specimen to thereby prevent uneven staining.

It is another object of the present invention to provide a pretreatment solution concentrate for immunohistochemical staining, which may easily be prepared into the pretreatment solution for immunohistochemical staining achieving the above objects.

Means for Solving the Problems

The present inventors have made intensive researches for achieving the above objects. First, researches were made for pretreatment solutions for immunohistochemical staining which are free of conventional organic solvents with safety concerns, such as xylene, benzene, or toluene, and which are mainly composed of water in consideration of environment and other factors. In this regard, researches were made on various surfactants as a component of the pretreatment solution which has both the effects of sufficiently eluting a paraffin-containing embedding medium from a glass slide with a tissue specimen embedded in the medium, and of inhibiting the eluted embedding medium from floating on the solution surface to disperse the medium in the solution, for allowing consecutive use of the pretreatment solution.

As a result, it was revealed that the above-mentioned two effects cannot be obtained simultaneously with only one surfactant, that the two effects may be attained to some extent with the use of two particular surfactants, but if the pretreatment solution is made alkaline and used three consecutive times or more, a staining reagent is likely to be repelled on the portion of a glass slide without a specimen to result in uneven staining in the staining step following use of the consecutively-used pretreatment solution.

Then, components which solve such problems were sought for by combining the two particular surfactants with various polymer compounds.

In addition, in order to confirm capability of simultaneous elution of the embedding medium and antigen retrieval in a single solution, and little effect on staining intensity in the staining step, various combinations of the components for solving the above problems were researched in combination with conventional antigen retrieval agents.

Further, researches were also made on cyclodextrin and derivatives thereof, which had not been used in a pretreatment solution for immunohistochemical staining, but were described in Patent Publication 1 to be able to remove residual surfactants when contained in a washing solution used after the pretreatment solution.

As a result, it was revealed through experiments that, when cyclodextrin or a derivative thereof is added at 2 mass % to a pretreatment solution along with the two particular surfactants mentioned above and an antigen retrieval agent, the action of the surfactants per se were inhibited possibly because of the binding with the surfactants as disclosed in Patent Publication 1, the dispersibility was remarkably deteriorated, and the problem of insoluble paraffin recurred, which should have been solved. Further, the staining intensity in the staining was significantly lowered and the expected effect could not be achieved. However, unexpectedly, it was confirmed that cyclodextrin or a derivative thereof at a particular content could prevent inhibition of the action of the surfactants, could inhibit deterioration of the staining intensity in the staining, and could solve various problems mentioned above.

It was further revealed that when an amphiphilic solution is added to the above-mentioned composition, the staining intensity was further enhanced, and the effect of inhibiting repelling of a staining reagent, which otherwise occurs when a pretreatment solution is alkaline, was further improved.

According to the present invention, there is provided a pretreatment solution for immunohistochemical staining for eluting a paraffin-containing embedding medium from a glass slide with a tissue specimen embedded in said medium, and for retrieving antigenicity of said tissue specimen, said pretreatment solution being usable three or more times, said pretreatment solution comprising an antigen retrieval agent, a polyoxyethylene alkyl phenyl ether nonionic surfactant, polyoxyethylene sorbitan nonionic surfactant, and cyclodextrin or a derivative thereof, with the balance being not less than 80 mass % of water, wherein a content of said antigen retrieval agent is such that a pH of said pretreatment solution is 5.0 to 10.0, and a content of said cyclodextrin or a derivative thereof is 0.01 to 1.0 mass %, and wherein said pretreatment solution optionally contains an amphiphilic solution.

According to the present invention, there is also provided a pretreatment solution concentrate for immunohistochemical staining comprising less water than the above-mentioned pretreatment solution for immunohistochemical staining, wherein said pretreatment solution is for use as the pretreatment solution for immunohistochemical staining at a predetermined pH by adding a predetermined amount of water thereto upon use.

According to the present invention, there is further provided the above-mentioned pretreatment solution concentrate for immunohistochemical staining, wherein said predetermined pH is 5.0 to 7.0, and wherein said pretreatment solution concentrate is supplied in single part.

According to the present invention, there is also provided the above-mentioned pretreatment solution concentrate for immunohistochemical staining, wherein said pretreatment solution concentrate is supplied in two parts and consists of a first solution concentrate comprising an antigen retrieval agent, and a second solution concentrate comprising a polyoxyethylene alkyl phenyl ether nonionic surfactant, a polyoxyethylene sorbitan nonionic surfactant, cyclodextrin or a derivative thereof, and optionally an amphiphilic solution, and wherein said pretreatment solution concentrate is for use by mixing said first solution concentrate, said second solution, concentrate, and a predetermined amount of water to set said predetermined pH to 8.0 to 10.0.

The pretreatment solution for immunohistochemical staining according to the present invention contains the antigen retrieval agent, the two particular surfactants, and the particular content of cyclodextrin or a derivative thereof, and not less than 80 mass % water as the balance. Thus the solution functions both to elute a paraffin-containing embedding medium used in immunohistochemical staining from a glass slide with a tissue specimen embedded in the medium, and to retrieve the antigenicity of the tissue specimen; allows for sufficient staining intensity in the subsequent immunohistochemical staining; maintains the eluted embedding medium dispersed therein even after the first use to prevent insoluble paraffin on the solution surface after use; and may be used three or more consecutive times. In addition, the present pretreatment solution, being free of organic solvents such as xylene, is excellently safe and environmentally advantageous. Further, even when made as an alkaline solution, the pretreatment solution for immunohistochemical staining according to the present invention still inhibits repelling of a staining reagent.

Therefore, by the use of the pretreatment solution for immunohistochemical staining according to the present invention, immunohistochemical staining may be conducted in a short time with less labor.

The pretreatment solution for immunohistochemical staining according to the present invention, when further contains an amphiphilic solution, allows for still more enhanced staining intensity, and provides still improved effect of inhibiting repelling of a staining reagent.

The pretreatment solution concentrate for immunohistochemical staining according to the present invention, containing less water than the pretreatment solution for immunohistochemical staining according to the present invention, may readily be used as the pretreatment solution for immunohistochemical staining at a predetermined pH by adding a predetermined amount of water upon use.

EMBODIMENTS OF THE INVENTION

The present invention will now be explained in detail.

The pretreatment solution for immunohistochemical staining and a solution concentrate thereof according to the present invention are for so-called immunohistochemical staining, wherein a specific substance (antigen) present in normal or tumor tissues or cells of living organisms is detected on the basis of a specific antigen-antibody reaction for pathological diagnosis.

Tissue specimens to be subjected to immunohistochemical staining have usually been fixed with formalin, alcohol, and the like, and embedded in an embedding medium containing paraffin for long-term storage. Such a formalin-fixed paraffin-embedded block is sectioned and adhered to a microscopic slide for immunohistochemical staining. Prior to the immunohistochemical staining, deparaffinization and antigen retrieval need to be conducted depending on the kind of the primary antigen to be used.

General procedures for the deparaffinization and the antigen retrieval include three steps, i.e., deparaffinizing, for example, a formalin-fixed paraffin-embedded tissue specimen, as mentioned above, with an organic solvent, such as xylene, benzene, or toluene; rehydrating the deparaffinized tissue specimen with an amphiphilic solution, such as ethanol; and retrieving antigens present on the rehydrated tissue specimen. After these steps, the immunohistochemical staining is conducted including washing and staining.

The present invention enables simultaneous conduct of the three-step pretreatment in a single solution, i.e., the pretreatment solution for immunohistochemical staining. Pretreatment solutions used in this way have hitherto been proposed and marketed, but most of them are for single use, and little of them may be used three or more consecutive times, for example, about three to four consecutive times. The present invention provides such a pretreatment solution and a solution concentrate thereof which may be used three times or more, preferably three to five times.

The pretreatment solution according to the present invention contains not less than 80 mass %, preferably not less than 85 mass %, more preferably not less than 90 mass % water, is free of generally used organic solvents with safety concerns, such as xylene, and contains an antigen retrieval agent, two particular nonionic surfactants, and cyclodextrin or a derivative thereof. The water is preferably deionized water. Here, this water content includes any moisture contents of other components.

The antigen retrieval agent is not particularly limited as long as it is conventional and enables retrieval of antigenicity by heat treatment, and those capable of pH adjustment depending on the tissue to be treated may suitably be selected. Examples of the antigen retrieval agent may include various buffer solutions such as citrate buffers, Tris buffers, SSC buffers, and these mixed with a chelating agent such as EDTA.

The content of the antigen retrieval agent may suitably be decided depending on the tissue to be treated so that the pH of the pretreatment solution of the present invention falls in the range of 5.0 to 10.0, preferably 6.0 to 9.0.

The two particular surfactants are polyoxyethylene (abbreviated as POE hereinbelow) alkyl phenyl ether nonionic surfactant and POE sorbitan nonionic surfactant.

In the pretreatment solution according to the present invention, the POE alkyl phenyl ether nonionic surfactant is mainly involved in deparaffinization, and may preferably be, for example, at least one of NP-40, Triton X-100, Triton X-114, or IGEPAL CA-630.

The content of the POE alkyl phenyl ether nonionic surfactant may suitably be decided taking the main function mentioned above into account, and is usually 0.01 to 1.0 mass %, preferably 0.01 to 0.5 mass %, more preferably 0.05 to 0.3 mass %. At too low a content of the POE alkyl phenyl ether nonionic surfactant, deparaffinization effect may be little, whereas at too high a content, it may be difficult to maintain a predetermined temperature in the heating for antigen retrieval to be discussed later.

In the pretreatment solution according to the present invention, the POE sorbitan nonionic surfactant is mainly involved in the function of maintaining the eluted paraffin dispersed therein during three or more times of use, through the interaction with cyclodextrin or a derivative thereof to be discussed later. The POE sorbitan nonionic surfactant may preferably be at least one of Tween 20, Tween 40, or Tween 80.

The content of the POE sorbitan nonionic surfactant may suitably be decided taking the main function mentioned above into account, and is usually 0.3 to 3.0 mass %, preferably 0.5 to 1.5 mass %, more preferably 0.5 to 1.0 mass %. At too low a content of the POE sorbitan nonionic surfactant, paraffin dispersibility in consecutive use may be deteriorated, whereas at too high a content, it may be difficult to maintain a predetermined temperature in the heating for antigen retrieval to be discussed later.

In the pretreatment solution according to the present invention, cyclodextrin or a derivative thereof is mainly involved in inhibiting a glass slide from repelling a staining reagent in the staining step following the pretreatment, and also in maintaining the eluted paraffin dispersed in the pretreatment solution. Cyclodextrin or a derivative thereof may be at least one of α-, β-, and γ-cyclodextrin, which are natural products, and derivatives thereof, in particular, with improved water solubility by the addition of a hydroxyl group and the like. Preferred examples may include hydroxyalkyl cyclodextrins, such as hydroxyalkyl-α-cyclodextrin, hydroxyalkyl-β-cyclodextrin, and hydroxyalkyl-γ-cyclodextrin, with hydroxyalkyl-β-cyclodextrin being particularly preferred. The alkyl may be, for example, ethyl or propyl.

The content of cyclodextrin or a derivative thereof is 0.01 to 1.0 mass %, preferably 0.05 to 0.5 mass %, more preferably 0.05 to 0.3 mass %. At a content of cyclodextrin or a derivative thereof of less than 0.01 mass %, the effect of inhibiting a glass slide from repelling a staining reagent cannot be achieved. On the other hand, at a content over 1.0 mass %, the above-mentioned effect of maintaining the eluted paraffin dispersed in the pretreatment solution is adversely affected, and the effect of the surfactants is inhibited. Also, antigen retrieval is inhibited, and sufficient staining intensity cannot be achieved. Thus, care must be taken of the upper limit of the content of cyclodextrin or a derivative thereof as the desired effect of the present invention may be inhibited.

The pretreatment solution according to the present invention may optionally contain other components in addition to the above-mentioned essential components, for the purpose of improving the desired effects, or exhibiting other effects without inhibiting the desired effects of the present invention.

As such other components, an amphiphilic solution may preferably be contained mainly for allowing for improved staining intensity in the staining following the pretreatment, and for further improving the effect of inhibiting a glass slide from repelling a staining reagent by the combination with cyclodextrin or a derivative thereof.

The amphiphilic solution is not particularly limited as long as the improvement of the above effects may be expected, and may preferably be, for example, at least one of ethylene glycol, propylene glycol, or 1,3-butylene glycol. Among these, ethylene glycol is particularly advantageous for use three or more consecutive times since, in addition to the improvement of the above effects, it has the effect of inhibiting the fine paraffin eluted and dispersed in the pretreatment solution from re-adhering to a glass slide.

The content of the amphiphilic solution, if any, in the pretreatment solution according to the present invention may suitably be decided taking its effect into account, and may usually be 1.0 to 5.0 mass %, preferably 2.0 to 4.0 mass %. At too low a content of the amphiphilic solution, the expected improvement in the effects may not be achieved, whereas at too high a content, the effect of inhibiting insoluble paraffin, which is one of the effects of the pretreatment solution of the present invention, may adversely be inhibited.

Other components may further include, other than the amphiphilic solution, at least one of preservatives and disinfectants, such as sodium azide, thimerosal, gentamicin, ProClin (trade name, manufactured by SUPELCO), p-hydroxybenzoates (paraben), benzalkonium chloride, and cetylpyridinium chloride. The content of such other components may suitably be selected taking their functions into account, as long as the effects of the present invention are not inhibited.

The pretreatment solution concentrate for immunohistochemical staining according to the present invention is for preparation of the above-mentioned pretreatment solution of the present invention, contains less water than the pretreatment solution of the present invention, and is for use at a predetermined pH by adding a predetermined amount of water thereto upon use.

The level of concentration may suitably be selected, and may usually be 5 to 20 folds, preferably 5 to 10 folds.

The pretreatment solution concentrate for immunohistochemical staining according to the present invention, when the predetermined pH is 5.0 to 7.0, is preferably supplied in single part for improved storage stability.

On the other hand, when the predetermined pH is 8.0 to 10.0, the pretreatment solution concentrate may be supplied in two parts, and composed of the first solution concentrate containing the antigen retrieval agent and optionally a preservative, and the second solution concentrate containing the polyoxyethylene alkyl phenyl ether nonionic surfactant, the polyoxyethylene sorbitan nonionic surfactant, cyclodextrin or a derivative thereof, and optionally an amphiphilic solution and a buffer.

The pretreatment solution concentrate for immunohistochemical staining according to the present invention, supplied either in single or two parts, may be prepared into the pretreatment solution of the present invention by mixing with a predetermined amount of water, such as deionized water, to set it to a predetermined pH.

The pretreatment solution according to the present invention may be used either in a manual process or in automated apparatus. In particular, use of temperature-control led automated apparatus or an automatic immunohistochemical stainer is convenient and preferred.

The pretreatment for immunohistochemical staining using the pretreatment solution of the present invention may be carried out, for example, by introducing a sample, such as a glass slide with tissue embedded in a paraffin-containing embedding medium to be treated, into the pretreatment solution of the present invention of which temperature is regulated to usually 20 to 70° C., preferably to not lower than the melting point of the embedding medium, such as paraffin, and shaking the system a plurality of times, for promoting deparaffinization. At this point, usually, removal of paraffin should be confirmed.

Next, the temperature of the pretreatment solution is raised for promoting antigen retrieval, under optional pressurization for shortening the reaction time. The temperature is usually 80 to 130° C., preferably 90 to 120° C., and the holding time at such temperatures is usually 1 to 70 minutes, preferably about 5 to 60 minutes.

After the treatment at a raised temperature, the temperature of the pretreatment solution is lowered again to about 20 to 70° C., and the system is shaken, to thereby complete the pretreatment.

The pretreatment solution according to the present invention may be used three or more, usually three to five, preferably three to four consecutive times, so that pretreatment of a next tissue specimen may be carried out similarly with a used pretreatment solution, and if the solution is designed for five-time use, similar staining results may be obtained from the first and the fifth pretreatment.

The pretreated glass slide may be subjected to immunohistochemical staining by performing the subsequent washing step and the immunohistochemical staining step through conventional methods.

EXAMPLES

The present invention will be explained in more detail with reference to Examples, Control Examples, and Comparative Examples, which do not limit the present invention.

In the Examples below, evaluations were made as follows:

Evaluation Item (1): Whether simultaneous deparaffinization and antigen retrieval in a single pretreatment solution is possible or not.

The evaluations were indicated as "Y" for those possible and "N" for those not possible.

Evaluation Item (2): Visual observation of insoluble paraffin on the solution surface after the deparaffinization and antigen retrieval with the pretreatment solution.

The evaluations were indicated as 5 points for those with no scum, 4 points for those with slight scum, 3 points for those with small masses of scum, 2 points for those with small and large masses of scum mixed, and 1 point for those with large masses of scum (the results are shown as an average of three times of use).

Evaluation Item (3): Visual observation of repelling of reagent for immunohistochemical staining on glass slide The evaluations were indicated as 5 points for those with no repelling, 4 points for those with a few fine repelling parts, 3 points for those with many fine repelling parts, 2 points for those with fine and large repelling parts mixed, and 1 point for those with large repelling parts or serious problems.

Evaluation Item (4): Staining intensity observed under optical microscope

The evaluations were indicated as 2 points for those with higher intensity compared to Control Examples 1 to 3, 1 point for those with slightly higher intensity compared to Control Examples 1 to 3, 0 points for those with intensity comparable to Control Examples 1 to 3, –1 points for those with slightly lower intensity compared to Control Examples 1 to 3, and –2 points for those with lower intensity compared to Control Examples 1 to 3.

Evaluation Item (5): Thickness of tissue after deparaffinization and antigen retrieval with pretreatment solution (the thinner the tissue, the more paraffin and the like present inside the tissue specimen has been eluted sufficiently.)

The evaluations were indicated as 5 points for those comparable with Control Examples 1 to 3, 4 points for those somewhat thicker compared to Control Examples 1 to 3, 3 points for those slightly thicker compared to Control Examples 1 to 3, 2 points for those thicker compared to Control Examples 1 to 3, and 1 point for those significantly thicker compared to Control Examples 1 to 3.

Evaluation Item (6): Whether or not three consecutive times of use of pretreatment solution are possible in view of Evaluation Items (1) to (5).

The evaluations were indicated as "Y" for those possible and "N" for those not possible.

Control Examples 1 to 3 (Deparaffinization, Rehydration, and Antigen Retrieval were Separately Conducted as Conventionally Done)

(A) Pretreatment
<Deparaffinization and Rehydration>

Formalin-fixed paraffin-embedded tonsillar tissue was sectioned at 3 μm, attached to a coated glass slide (MAS coat, manufactured by MATSUNAMI GLASS IND., LTD.), and dried at 37° C. for 18 hours. The slide was deparaffinized by three-minute standing in a xylene layer three times, and then rehydrated by three-minute standing in an ethanol layer four times. After the final standing in the ethanol layer, the slide was washed in a phosphate buffer at pH 7.6 three times for three-minutes each.

<Antigen Retrieval>

The rehydrated and washed glass slide was placed in a heat-resistant container filled with a pH 6.0 citrate buffer (Control Example 1), a pH 7.0 citrate buffer (Control Example 2), or a pH 9.0 Tris-HCl buffer containing EDTA (Control Example 3), wherein neither of the buffers contained surfactants. Each heat-resistant container was placed in a desktop autoclave (manufactured by ALP CO., LTD.) and autoclaved at 121° C. for 20 minutes. After the autoclaving, each heat-resistant container was taken out and left to stand at room temperature for 20 minutes to retrieve antigenicity.

(B) Washing

After completion of the 20-minute standing, the glass slide was transferred into a pH 7.6 phosphate buffer and washed by five-minute standing three times.

(C) Immunohistochemical Staining
(1) Manual Immunohistochemical Staining

A glass slide undergone washing step (B) was placed in a 3% hydrogen peroxide/methanol solution, lightly shaken, and left to stand for 10 minutes. Then the slide was transferred into a pH 7.6 phosphate buffer, and washed by five-minute standing three times.

Moisture was removed from the resulting glass slide, and a circle was drawn with PAP PEN (manufactured by DAIDO SANGYO CO., LTD.) around the tissue specimen. Then, as a primary antibody, CD3 rabbit monoclonal antibody (SP7) (trade name, manufactured by NICHIREI BIOSCIENCES INC.) was added dropwise to the glass slide, and reacted at 25° C. for 60 minutes. After completion of the reaction, the slide was transferred into a pH 7.6 phosphate buffer, and washed by five-minutes standing three times.

Then moisture was removed from the washed glass slide, and Histofine Simple Stain MAX-PO (MULTI) (trade name, manufactured by NICHIREI BIOSCIENCES INC.) as a secondary antibody was added dropwise to the slide, and reacted at 25° C. for 30 minutes. After completion of the reaction, the slide was transferred into a pH 7.6 phosphate buffer, and washed by five-minute standing three times.

After the washing, DAB solution prepared using DAB substrate kit (trade name, manufactured by NICHIREI BIOSCIENCES INC.) as a chromogenic substrate was added dropwise to the glass slide deprived of moisture, and reacted at room temperature for five-minutes. The slide was washed in running water for five-minutes, deprived of moisture, reacted with Mayer's hematoxylin for 30 seconds for color development, and washed in running water for five-minutes.

Then moisture was removed, and the slide was subjected to dehydration and clearing by passage through an ethanol layer three times, three-minute standing in an ethanol layer once, passage through a xylene layer once, and five-minute standing in a xylene layer twice, and then mounted in a non-aqueous mounting medium (manufactured by NICHIREI BIOSCIENCES INC.).

(2) Immunohistochemical Staining in Automatic Immunohistochemical Stainer

The glass slide undergone washing step (B) was set in a slide rack of an automatic immunohistochemical stainer, HISTOSTAINER (trade name, manufactured by NICHIREI BIOSCIENCES INC.) (referred to as HISTOSTAINER hereinbelow). The tissue was covered with a pH 7.6 phosphate buffer so as not to be dried. The slide set in the apparatus was washed in PBS for HISTOSTAINER, and air-dried. A three-percent hydrogen peroxide solution (manufactured by NICHIREI BIOSCIENCES INC.) was added dropwise to the slide in the apparatus, and reacted for five-minutes.

After completion of the reaction, the slide was washed in PBS for HISTOSTAINER, and air-dried. CD3 rabbit monoclonal antibody (SP7) (for HISTOSTAINER) (trade name, manufactured by NICHIREI BIOSCIENCES INC.) as a primary antibody was added dropwise to the slide, and reacted at room temperature for 30 minutes. After completion of the reaction, the slide was washed twice in PBS for HISTOSTAINER. After air-drying, HISTOFINE SIMPLE STAIN MAX-PO (MULTI) (for HISTOSTAINER) (trade name, manufactured by NICHIREI BIOSCIENCES INC.) as a secondary antibody was added dropwise to the slide, and reacted at room temperature for 30 minutes. After completion of the reaction, the slide was washed twice in PBS for HISTOSTAINER.

Next, a DAB solution as a chromogenic substrate prepared using DAB substrate kit (for HISTOSTAINER) (trade name, manufactured by NICHIREI BIOSCIENCES INC.) was added dropwise to the slide, and reacted at room temperature for 10 minutes. After completion of the reaction, the slide was washed once in PBS for HISTOSTAINER, and rinsed once in water. The stained slide was taken out, and washed in running water for five-minutes. After that, moisture was removed, and Mayer's hematoxylin was acted on the slide for 30 seconds, followed by washing in running water for five-minutes.

Then moisture was removed, and the slide was subjected to dehydration and clearing by passage through an ethanol layer three times, three-minute standing in an ethanol layer once, passage through a xylene layer once, and five-minute standing in a xylene layer twice, and then mounted in a non-aqueous mounting medium (manufactured by NICHIREI BIOSCIENCES INC.).

Example 1: Preparation of Pretreatment Solution, at pH 9.0, without Amphiphilic Solution A tenfold solution concentrate of a Tris-HCl buffer containing EDTA was prepared and filtered through a 0.22 μm filter, with which buffer, when a pretreatment solution concentrate to be prepared below was diluted tenfold, the pH of the resulting pretreatment solution could be 9.0. To the tenfold solution concentrate thus obtained were added Triton X-100 at a final concentration of 0.1 mass % and Tween 20 at a final concentration of 1.0 mass %, both nonionic surfactants, and hydroxypropyl-β-cyclodextrin at a final concentration of 0.1 mass %, to thereby prepare a pretreatment solution concentrate.

The pretreatment solution concentrate thus prepared was diluted tenfold with deionized water to obtain a pretreatment solution.

(A) Pretreatment
<Deparaffinization and Antigen Retrieval>

The pretreatment solution prepared above was placed in a temperature-controlled automatic apparatus, PTModule (trade name, manufactured by THERMO FISHER SCIENTIFIC K.K.) (abbreviated as PTModule hereinbelow), and heated to 65° C.

On the other hand, formalin-fixed paraffin-embedded tonsillar tissue was sectioned at 3 μm, attached to a coated glass slide (MAS coat, manufactured by MATSUNAMI GLASS IND., LTD.), and dried at 37° C. for 18 hours. The slide was set in a slide rack of an automatic immunohistochemical stainer, HISTOSTAINER.

When the temperature of the solution in the PTModule reached 65° C., the cover was opened, and the slide rack in which the slide had been set was placed in the solution, and shaken several times. The rack was drawn out of the solution to confirm that no paraffin was left on the slide, and then set in the PTModule, and the cover was closed. The slide was heat treated in the PTModule according to a preset program (the solution temperature was raised from 65° C. up to 100° C., held at 100° C. for 40 minutes, and lowered down to 65° C.).

(B) Washing

After completion of the heat treatment, the slide, while set in the slide rack, was lightly shaken, then transferred into a pH 7.6 phosphate buffer containing 0.05 mass % Tween 20, and left to stand for five-minutes. Visual observations were made for any residual paraffin on the tissue specimen or the slide (whether any residual paraffin which could not be removed by washing was observed), and for any insoluble paraffin on the solution surface after the pretreatment solution was left to cool to room temperature after the pretreatment.

(C) Immunohistochemical Staining in Automatic Immunohistochemical Stainer

The glass slide set in the rack for HISTOSTAINER and undergone washing step (B) was set in HISTOSTAINER as it was, washed in PBS for HISTOSTAINER, and air-dried. A three-percent hydrogen peroxide solution (manufactured by NICHIREI BIOSCIENCES INC.) was added dropwise to the slide, and reacted for five-minutes.

After completion of the reaction, the slide was washed in PBS for HISTOSTAINER, and air-dried. CD3 rabbit monoclonal antibody (SP7) (for HISTOSTAINER) (trade name, manufactured by NICHIREI BIOSCIENCES INC.) as a primary antibody was added dropwise to the slide, and reacted at room temperature for 30 minutes. After completion of the reaction, the slide was washed twice in PBS for HISTOSTAINER. After air-drying, HISTOFINE SIMPLE STAIN MAX-PO (MULTI) (for HISTOSTAINER) (trade name, manufactured by NICHIREI BIOSCIENCES INC.) as a secondary antibody was added dropwise to the slide, and reacted at room temperature for 30 minutes. After completion of the reaction, the slide was washed twice in PBS for HISTOSTAINER.

Next, a DAB solution as a chromogenic substrate prepared using DAB substrate kit (for HISTOSTAINER) (trade name, manufactured by NICHIREI BIOSCIENCES INC.) was added dropwise to the slide, and reacted at room temperature for 10 minutes. After completion of the reaction, the slide was washed once in PBS for HISTOSTAINER, and rinsed once in water. The stained slide was taken out, and washed in running water for five-minutes. After that, moisture was removed, and Mayer's hematoxylin was acted on the slide for 30 seconds, followed by washing in running water for five-minutes.

Moisture was removed, and the slide was subjected to dehydration and clearing by passage through an ethanol layer three times, three-minute standing in an ethanol layer once, passage through a xylene layer once, and five-minute standing in a xylene layer twice, and then mounted in a non-aqueous mounting medium (manufactured by NICHIREI BIOSCIENCES INC.).

Above steps (A) to (C) were repeated three times without changing the pretreatment solution. The results of the evaluations mentioned above at the third time are shown in Table 1 together with those of Control Examples 1 to 3, which were the results of one treatment.

Example 2: Preparation of Pretreatment Solution, at pH 9.0, Containing Amphiphilic Solution A tenfold solution concentrate of a Tris-HCl buffer containing EDTA was prepared and filtered through a 0.22 µm filter, with which buffer, when a pretreatment solution concentrate to be prepared below was diluted tenfold, the pH of the resulting pretreatment solution could be at 9.0. To the tenfold solution concentrate thus obtained were added Triton X-100 at a final concentration of 0.1 mass % and Tween 20 at a final concentration of 1.0 mass %, both nonionic surfactants, hydroxypropyl-β-cyclodextrin at a final concentration of 0.1 mass %, and ethylene glycol at a final concentration of 3.0 mass %, to thereby prepare a pretreatment solution concentrate.

The pretreatment solution concentrate thus prepared was diluted tenfold with deionized water to obtain a pretreatment solution.

Then steps (A) to (C) were carried out and the evaluations were made in the same way as in Example 1, except that the pretreatment solution was replaced with the one obtained above. The results are shown in Table 1.

Incidentally, evaluations were also made in the same way as in Example 2 with β-, β- or γ-cyclodextrin in place of hydroxypropyl-β-cyclodextrin, to obtain similar results. It was revealed that hydroxypropyl-β-cyclodextrin was most preferred in view of easiness of handling, since α- and β-cyclodextrin were not soluble at room temperature and their effects were not exhibited until dissolved upon the heat treatment.

Example 3: Preparation of Pretreatment Solution, at pH 6.0, without Amphiphilic Solution A tenfold solution concentrate of a citrate buffer was prepared and filtered through a 0.22 µm filter, with which buffer, when a pretreatment solution concentrate to be prepared below was diluted tenfold, the pH of the resulting pretreatment solution could be at 6.0. To the tenfold solution concentrate thus obtained were added Triton X-100 at a final concentration of 0.1 mass % and Tween 20 at a final concentration of 1.0 mass %, both nonionic surfactants, hydroxypropyl-β-cyclodextrin at a final concentration of 0.1 mass %, and ethylene glycol at a final concentration of 3.0 mass %, to thereby prepare a pretreatment solution concentrate.

The pretreatment solution concentrate thus prepared was diluted tenfold with deionized water to obtain a pretreatment solution.

Then steps (A) to (C) were carried out and the evaluations were made in the same way as in Example 1, except that the pretreatment solution was replaced with the one obtained above. The results are shown in Table 1.

Example 4: Preparation of Pretreatment Solution, at pH 6.0, Containing Amphiphilic Solution A tenfold solution concentrate of a citrate buffer was prepared and filtered through a 0.22 µm filter, with which buffer, when a pretreatment solution concentrate to be prepared below was diluted tenfold, the pH of the resulting pretreatment solution could be at 6.0. To the tenfold solution concentrate thus obtained were added Triton X-100 at a final concentration of 0.1 mass % and Tween 20 at a final concentration of 1.0 mass %, both nonionic surfactants, hydroxypropyl-β-cyclodextrin at a final concentration of 0.1 mass %, and ethylene glycol at a final concentration of 3.0 mass %, to thereby prepare a pretreatment solution concentrate.

The pretreatment solution concentrate thus prepared was diluted tenfold with deionized water to obtain a pretreatment solution.

Then steps (A) to (C) were carried out and the evaluations were made in the same way as in Example 1, except that the pretreatment solution was replaced with the one obtained above. The results are shown in Table 1.

Example 5: Preparation of Pretreatment Solution, at pH 7.0, without Amphiphilic Solution A tenfold solution concentrate of a citrate buffer containing sodium hydroxide was prepared and filtered through a 0.22 µm filter, with which buffer, when a pretreatment solution concentrate to be prepared below was diluted tenfold, the pH of the resulting pretreatment solution could be at 7.0. To the tenfold solution concentrate thus obtained were added Triton X-100 at a final concentration of 0.1 mass % and Tween 20 at a final concentration of 1.0 mass %, both nonionic surfactants, hydroxypropyl-β-cyclodextrin at a final concentration of 0.1 mass %, and ethylene glycol at a final concentration of 3.0 mass %, to thereby prepare a pretreatment solution concentrate.

The pretreatment solution concentrate thus prepared was diluted tenfold with deionized water to obtain a pretreatment solution.

Then steps (A) to (C) were carried out and the evaluations were made in the same way as in Example 1, except that the pretreatment solution was replaced with the one obtained above. The results are shown in Table 1.

Example 6: Preparation of Pretreatment Solution, at pH 7.0, Containing Amphiphilic Solution A tenfold solution concentrate of a citrate buffer containing sodium hydroxide was prepared and filtered through a 0.22 µm filter, with which buffer, when a pretreatment solution concentrate to be prepared below was diluted tenfold, the pH of the resulting pretreatment solution could be at 7.0. To the tenfold solution concentrate thus obtained were added Triton X-100 at a final concentration of 0.1 mass % and Tween 20 at a final concentration of 1.0 mass %, both nonionic surfactants, hydroxypropyl-β-cyclodextrin at a final concentration of 0.1 mass %, and ethylene glycol at a final concentration of 3.0 mass %, to thereby prepare a pretreatment solution concentrate.

The pretreatment solution concentrate thus prepared was diluted tenfold with deionized water to obtain a pretreatment solution.

Then steps (A) to (C) were carried out and the evaluations were made in the same way as in Example 1, except that the pretreatment solution was replaced with the one obtained above. The results are shown in Table 1.

Comparative Example 1: Preparation of Pretreatment Solution, at pH 9.0, without Amphiphilic Solution and Cyclodextrin A tenfold solution concentrate of a Tris-HCl buffer containing EDTA was prepared and filtered through a 0.22 µm filter, with which buffer, when a pretreatment solution concentrate to be prepared below was diluted tenfold, the pH of the resulting pretreatment solution could be at 9.0. To the tenfold solution concentrate thus obtained were added Triton X-100 at a final concentration of 0.1 mass % and Tween 20 at a final concentration of 1.0 mass %, both nonionic surfactants, to thereby prepare a pretreatment solution concentrate.

The pretreatment solution concentrate thus prepared was diluted tenfold with deionized water to obtain a pretreatment solution.

Then steps (A) to (C) were carried out and the evaluations were made in the same way as in Example 1, except that the pretreatment solution was replaced with the one obtained above. Incidentally, the pretreatment solution of Comparative Example 1 could not be used consecutively, so that the results of the second use are shown in Table 1.

Comparative Example 2: Preparation of Pretreatment Solution, at pH 9.0, without Cyclodextrin A tenfold solution concentrate of a Tris-HCl buffer containing EDTA was prepared and filtered through a 0.22 μm filter, with which buffer, when a pretreatment solution concentrate to be prepared below was diluted tenfold, the pH of the resulting pretreatment solution could be at 9.0. To the tenfold solution concentrate thus obtained were added Triton X-100 at a final concentration of 0.1 mass % and Tween 20 at a final concentration of 1.0 mass %, both nonionic surfactants, and ethylene glycol at a final concentration of 3.0 mass %, to thereby prepare a pretreatment solution concentrate.

The pretreatment solution concentrate thus prepared was diluted tenfold with deionized water to obtain a pretreatment solution.

Then steps (A) to (C) were carried out and the evaluations were made in the same way as in Example 1, except that the pretreatment solution was replaced with the one obtained above.

Comparative Examples 3 and 4: Preparation of Pretreatment Solution, at pH 9.0, without Cyclodextrin Pretreatment solutions were prepared in the same way as in Comparative Example 2, except that ethylene glycol was replaced with propylene glycol (Comparative Example 3) or 1,3-butylene glycol (Comparative Example 4), and steps (A) to (C) were carried out and the evaluations were made in the same way as in Example 1.

The results shown in Table 1 demonstrate that the pretreatment solutions of Comparative Examples 1 to 4 without cyclodextrin could not be used consecutively in view of the slides repelling the staining reagent (Evaluation Item (3)). With the pretreatment solutions of Comparative Examples 2 to 4 containing an amphiphilic solution, the repelling was slightly resolved compared to Comparative Example 1, but the pretreatment solutions did not have properties to withstand the use three or more consecutive times. In contrast, the pretreatment solutions of the Examples could be used three consecutive times. In particular, it is seen that, with an amphiphilic solution, the staining intensity (Evaluation Item (4)) tended to be improved more.

Incidentally, it was confirmed that, in Example 2, when Triton X-100 was replaced with NP-40, Triton X-114, or IGEPAL CA-630, and Tween 20 was replaced with Tween 40 or Tween 80, similar effects were achieved.

Referential Comparative Example 1: Preparation of Pretreatment Solution, at pH 9.0, Examination with One Nonionic Surfactant A tenfold solution concentrate of a Tris-HCl buffer containing EDTA was prepared and filtered through a 0.22 μm filter, with which buffer, when a pretreatment solution concentrate to be prepared below was diluted tenfold, the pH of the resulting pretreatment solution could be at 9.0. To the tenfold solution concentrate thus obtained was added each of the nonionic surfactants as shown in Table 2 at a final concentration of 0.1 mass %, to thereby prepare pretreatment solution concentrates.

Each of the pretreatment solution concentrates thus prepared was diluted tenfold with deionized water to obtain a pretreatment solution.

Then steps (A) to (C) were carried out once and evaluations were made with regard to Evaluation Items (1) to (4) in the same way as in Example 1, except that the pretreatment solution was replaced with the ones obtained above. The results are shown in Table 2.

TABLE 1

| | Evaluation Item (1) | Evaluation Item (2) | Evaluation Item (3) | Evaluation Item (4) | Evaluation Item (5) | Evaluation Item (6) |
|---|---|---|---|---|---|---|
| Control Example 1 | — | — | 5 points | 0 point | 5 points | — |
| Control Example 2 | — | — | 5 points | 0 point | 5 points | — |
| Control Example 3 | — | — | 5 points | 0 point | 5 points | — |
| Example 1 | Y | 5 points | 4 points | 0 point | 4 points | Y |
| Example 2 | Y | 4.5 points | 4 points | 2 points | 4 points | Y |
| Example 3 | Y | 4.5 points | 5 points | 0 point | 4 points | Y |
| Example 4 | Y | 4.5 points | 5 points | 2 points | 4 points | Y |
| Example 5 | Y | 4.5 points | 5 points | 0 point | 4 points | Y |
| Example 6 | Y | 4.5 points | 5 points | 2 points | 4 points | Y |
| Comparative Example 1 | Y | 5 points | 1 point | 0 point | 4 points | N |
| Comparative Example 2 | Y | 4.5 points | 2 points | 2 points | 4 points | N |
| Comparative Example 3 | Y | 4 points | 2 points | 0 point | 4 points | N |
| Comparative Example 4 | Y | 4 points | 2 points | 1 point | 4 points | N |

TABLE 2

| Kind of Surfactant | Evaluation Item (1) | Evaluation Item (2) | Evaluation Item (3) | Evaluation Item (4) |
|---|---|---|---|---|
| Triton X-100 | Y | 1 point | 2 points | 0 point |
| NP-40 | Y | 1 point | 2 points | 0 point |
| Triton X-114 | Y | 1 point | 2 points | 0 point |
| Tween 20 | N | 4 points | 1 point | −1 point |
| Tween 40 | N | 4 points | 1 point | −1 point |
| Tween 80 | N | 4 points | 1 point | −1 point |

The results shown in Table 2 demonstrate that the consecutive use cannot be realized with only one surfactant.

Referential Comparative Example 2: Preparation of Pretreatment Solution, at pH 9.0, Examination with Two Nonionic Surfactants A tenfold solution concentrate of a Tris-HCl buffer containing EDTA was prepared and filtered through a 0.22 μm filter, with which buffer, when a pretreatment solution concentrate to be prepared below was diluted tenfold, the pH of the resulting pretreatment solution could be at 9.0. To the tenfold solution concentrate thus obtained were added Triton X-100 at a final concentration of 0.1 mass % and Tween 20 at each final concentration as shown in Table 2, both nonionic surfactants, to thereby prepare pretreatment solution concentrates.

Each of the pretreatment solution concentrates thus prepared was diluted tenfold with deionized water to obtain a pretreatment solution.

Then steps (A) to (C) were carried out twice and evaluations were made with regard to Evaluation Items (1) to (5) in the same way as in Example 1, except that the pretreatment solution was replaced with the ones obtained above. The results of the second time are shown in Table 3.

TABLE 3

| Final Concentration of Tween 20 | Evaluation Item (1) | Evaluation Item (2) | Evaluation Item (3) | Evaluation Item (4) | Evaluation Item (5) |
|---|---|---|---|---|---|
| 0.1 mass % | Y | 2 points | 1 point | 0 point | 3 points |
| 0.3 mass % | Y | 3 points | 1 point | 0 point | 3 points |
| 0.5 mass % | Y | 4 points | 1 point | 0 point | 4 points |
| 1.0 mass % | Y | 5 points | 1 point | 0 point | 4 points |
| 2.0 mass % | Y | 5 points | 1 point | 0 point | 4 points |
| 3.0 mass % | Y | 5 points | 1 point | 0 point | 4 points |

The results shown in Table 3 demonstrate that the consecutive use cannot be realized even with the two particular surfactants.

Examples 7 to 10 and Comparative Examples 5 and 6: Examination on Cyclodextrin Content Pretreatment solutions were prepared and the evaluations were made in the same way as in Example 2, except that the final concentration of hydroxypropyl-β-cyclodextrin of 0.1 mass % was changed to the final concentration of 0.01 mass % (Example 7), 0.05 mass % (Example 8), 0.5 mass % (Example 9), 1.0 mass % (Example 10), 2.0 mass % (Comparative Example 5), or 15.0 mass % (Comparative Example 6). The results are shown in Table 4 together with those of Example 2.

TABLE 4

| | Final Concentration of Hydroxypropyl-β-cyclodextrin | Evaluation Item (1) | Evaluation Item (2) | Evaluation Item (3) | Evaluation Item (4) | Evaluation Item (5) | Evaluation Item (6) |
|---|---|---|---|---|---|---|---|
| Example 2 | 0.1 mass % | Y | 4.5 points | 4 points | 2 points | 4 points | Y |
| Example 7 | 0.01 mass % | Y | 4 points | 3 points | 2 points | 4 points | Y |
| Example 8 | 0.05 mass % | Y | 4 points | 3.5 points | 2 points | 4 points | Y |
| Example 9 | 0.5 mass % | Y | 4 points | 4 points | 1 point | 4 points | Y |
| Example 10 | 1.0 mass % | Y | 3.5 points | 4.5 points | 0 point | 4 points | Y |
| Comparative Example 5 | 2.0 mass % | Y | 2.5 points | 4.8 points | −1 point | 4 points | N |
| Comparative Example 6 | 15.0 mass % | Y | 2 points | 5 points | −1 point | 4 points | N |

The results shown in Table 4 demonstrate that if the content of cyclodextrin, even if contained, is out of the particular range, the effect of realizing the consecutive use cannot be obtained.

Example 11: Example of Pretreatment Solution Concentrate Supplied in Two Parts

Solution A was prepared composed of a tenfold solution concentrate of a 500 mM Tris-HCl buffer containing 100 mM EDTA, with which buffer, when a pretreatment solution concentrate to be prepared below was diluted tenfold, the pH of the resulting pretreatment solution could be at 9.0, and 0.01 mass % sodium azide as a preservative.

On the other hand, Solution B was prepared composed of a 1 mM citrate buffer, 1 mass % Triton X-100 and 10 mass % Tween 20, both nonionic surfactants, 1 mass % hydroxypropyl-β-cyclodextrin, and 30 mass % ethylene glycol.

Solutions A and B were mixed with deionized water at 1:1:8 to prepare a pretreatment solution at pH 9.0.

The evaluations of the obtained pretreatment solution were made in the same way as in Example 2. It was revealed that results similar to those of Example 2 were obtained with regard to all Evaluation Items.

Referential Comparative Example 3: Examination with Polysaccharides, Carbohydrate Polymers, or High Polymers in Place of Cyclodextrin Pretreatment solutions were prepared in the same way as in Example 1, except that hydroxypropyl-β-cyclodextrin was replaced with various polysaccharides, carbohydrate polymers, or high polymers shown in Table 5.

The pretreatment solutions thus obtained were evaluated with regard to Evaluation Items (1) to (3) and (6) in the same way as in Example 1. The results are shown in Table 5.

TABLE 5

| Polymer in place of hydroxypropyl-β-cyclodextrin | Evaluation Item (1) | Evaluation Item (2) | Evaluation Item (3) | Evaluation Item (6) |
|---|---|---|---|---|
| Dextran (Mw. 35000-45000) (1 mass %) | N | 1 point | 1 point | N |
| Dextran (Mw. 400000-500000) (1 mass %) | N | 1 point | 1 point | N |
| Dextran (Mw. 2000000) (1 mass %) | Y | 2 points | 3 points | N |
| Dextran (Mw. 5000000-20000000) (1 mass %) | Y | 1 point | 3 points | N |
| D-sorbitol (1 mass %) | N | 1 point | 2 points | N |
| Trehalose (1 mass %) | N | 1 point | 2 points | N |
| PVP (Mw. 58000) (1 mass %) | Y | 4 points | 2 points | N |
| PVP (Mw. 58000) (5 mass %) | Y | 4 points | 2 points | N |
| PVP (Mw. 34000) (1 mass %) | Y | 4 points | 2 points | N |
| PVP (Mw. 130000) (1 mass %) | Y | 3 points | 1 point | N |
| PVP/VA (Mw. 58000) (1 mass %) | Y | 4 points | 2 points | N |
| PVP/VA (Mw. 58000) (3 mass %) | Y | 4 points | 2 points | N |
| PVP/VA (Mw. 58000) (5 mass %) | Y | 4 points | 2 points | N |

PVP: polyvinyl pyrrolidone
PVP/VA: polyvinyl pyrrolidone-vinyl acetate copolymer The results shown in Table 5 demonstrate that, among dextrins having linear sugars, when those having relatively low molecular weights, a monosaccharide such as sorbitol, or a disaccharide such as trehalose is contained in the pretreatment solution, deparaffinization could not be effected, which was otherwise effected. It is assumed that the effects of Tween 20 or Triton X-100 were inhibited by these components. On the other hand, dextrans having high molecular weights were found to give off odor when heated.

PVP and copolymers thereof are used as drug excipients for dispersing water-insoluble substances. In expectation of such effect, some PVPs were examined, and the results as shown in Table 5 above indicate that good results were achieved with regard to insoluble paraffin (Evaluation Item (2)), but results sufficient for consecutive use were not achieved with regard to repelling of the staining reagent on the slides (Evaluation Item (3)). It was also revealed that PVP of a higher molecular weight had higher viscosity, and thus was inconvenient to use.

What is claimed is:

1. A method for immunohistochemical staining of a paraffin-embedded tissue sample, which comprises steps of:
   (a) contacting the paraffin-embedded tissue sample with a pretreatment solution of a pH of 5.0-10.0 at a first temperature range of 20 to 70° C. to promote deparaffinization and then the temperature is raised to a second temperature range of 80 to 130° C. to promote antigen retrieval to provide a deparaffinized and antigen-retrieved tissue sample;
   (b) washing the deparaffinized and antigen-retrieved tissue sample obtained in (a) with said pretreatment solution; and
   (c) immunohistochemical staining the washed tissue sample,
   wherein said pretreatment solution comprises a pH buffer, two nonionic surfactants, and cyclodextrin or a derivative thereof, with the balance being not less than 80 mass % of water;
   wherein said two nonionic surfactants are a polyoxyethylene alkyl phenyl ether nonionic surfactant and a polyoxyethylene sorbitan nonionic surfactant, a content of said polyoxyethylene alkyl phenyl ether nonionic surfactant being 0.01 to 1.0 mass %, and a content of said polyoxyethylene sorbitan nonionic surfactant being 0.3 to 3.0 mass %,
   wherein said pH buffer is selected from the group consisting of a citrate buffer, a citrate buffer mixed with a chelating agent, and a Tris buffer mixed with a chelating agent, and a content of said pH buffer being such that a pH of said pretreatment solution is 5.0 to 10.0; and
   wherein a content of said cyclodextrin or a derivative thereof is 0.01 to 1.0 mass %.

2. The method according to claim 1, wherein said pretreatment solution further comprises at least one amphiphilic substance selected from the group consisting of ethylene glycol, propylene glycol, and 1, 3-butylene glycol.

3. The method according to claim 2, wherein a content of said amphiphilic substance is 1.0 to 5.0 mass % based on the total mass of said pretreatment solution.

4. The method according to claim 1, wherein said polyoxyethylene alkyl phenyl ether nonionic surfactant is at least one selected from the group consisting of NP-40, Triton X-100, Triton X-114, and IGEPAL CA-630, and said polyoxyethylene sorbitan nonionic surfactant is at least one selected from the group consisting of Tween 20, Tween 40, and Tween 80.

5. The method according to claim 1, wherein said cyclodextrin or a derivative thereof is at least one selected from the group consisting of α-cyclodextrin, β-cyclodextrin, γ-cyclodextrin, hydroxyalkyl-α-cyclodextrin, hydroxyalkyl-β-cyclodextrin, and hydroxyalkyl-γ-cyclodextrin.

6. The method according to claim 1, wherein, in said step (a), a duration of the second temperature range is 1 to 70 minutes, during which the pretreatment solution is under pressurization; and wherein said step (a) further comprises lowering the temperature to 20 to 70° C. after antigen retrieval.

7. The method according to claim 1, which further comprises, before said step (a),
   a step of preparing a pretreatment solution concentrate containing said pH buffer, said two nonionic surfactants, and said cyclodextrin or a derivative thereof, and
   a step of adding water to said pretreatment solution concentrate to prepare said pretreatment solution,
   wherein a content of said pH buffer in thus prepared pretreatment solution is such that a pH of said pretreatment solution is 5.0 to 7.0.

8. The method according to claim 7, wherein said pretreatment solution concentrate further comprises at least one amphiphilic substance selected from the group consisting of ethylene glycol, propylene glycol, and 1, 3-butylene glycol.

9. The method according to claim 7, wherein said polyoxyethylene alkyl phenyl ether nonionic surfactant is selected from the group consisting of NP-40, Triton X-100, Triton X-114, and IGEPAL CA-630, and said polyoxyethylene sorbitan nonionic surfactant is selected from the group consisting of Tween 20, Tween 40, and Tween 80.

10. The method according to claim 7, wherein said cyclodextrin or a derivative thereof is at least one selected from the group consisting of α-cyclodextrin, β-cyclodextrin, γ-cyclodextrin, hydroxyalkyl-α-cyclodextrin, hydroxyalkyl-β-cyclodextrin, and hydroxyalkyl-γ-cyclodextrin.

11. The method according to claim 1, which further comprises, before said step (a),
   a step of preparing a first solution concentrate containing said pH buffer, and a second solution concentrate containing said two nonionic surfactants, and said cyclodextrin or a derivative thereof, and
   a step of mixing said first solution concentrate, said second solution concentrate, and water to prepare said pretreatment solution,
   wherein a content of said pH buffer in thus prepared pretreatment solution is such that a pH of said pretreatment solution is 8.0 to 10.0.

12. The method according to claim 11, wherein said second solution concentrate further comprises at least one amphiphilic substance selected from the group consisting of ethylene glycol, propylene glycol, and 1, 3-butylene glycol.

13. The method according to claim 11, wherein said polyoxyethylene alkyl phenyl ether nonionic surfactant is at least one selected from the group consisting of NP-40, Triton X-100, Triton X-114, and IGEPAL CA-630, and said polyoxyethylene sorbitan nonionic surfactant is at least one selected from the group consisting of Tween 20, Tween 40, and Tween 80.

14. The method according to claim 11, wherein said cyclodextrin or a derivative thereof is at least one selected from the group consisting of α-cyclodextrin, β-cyclodextrin, γ-cyclodextrin, hydroxyalkyl-α-cyclodextrin, hydroxyalkyl-β-cyclodextrin, and hydroxyalkyl-γ-cyclodextrin.

* * * * *